United States Patent
Britt et al.

(10) Patent No.: US 10,605,778 B2
(45) Date of Patent: Mar. 31, 2020

(54) GAS SENSOR INCORPORATING A TEMPERATURE-CONTROLLED SENSING MATERIAL

(71) Applicant: MATRIX SENSORS, INC., San Diego, CA (US)

(72) Inventors: David K Britt, El Cerrito, CA (US); Paul R Wilkinson, Carlsbad, CA (US); Steven Yamamoto, San Diego, CA (US)

(73) Assignee: MATRIX SENSORS, INC., San Diego, CA (US)

(*) Notice: Subject to any disclaimer, the term of this patent is extended or adjusted under 35 U.S.C. 154(b) by 22 days.

(21) Appl. No.: 16/118,159

(22) Filed: Aug. 30, 2018

(65) Prior Publication Data

US 2019/0072523 A1    Mar. 7, 2019

Related U.S. Application Data

(60) Provisional application No. 62/553,756, filed on Sep. 1, 2017.

(51) Int. Cl.

| | |
|---|---|
| *G01N 29/02* | (2006.01) |
| *G01N 29/036* | (2006.01) |
| *G01N 29/32* | (2006.01) |
| *G01N 33/00* | (2006.01) |
| *G01N 29/22* | (2006.01) |

(52) U.S. Cl.
CPC ......... *G01N 29/022* (2013.01); *G01N 29/036* (2013.01); *G01N 29/222* (2013.01); *G01N 29/326* (2013.01); *G01N 33/004* (2013.01); *G01N 33/0016* (2013.01); *G01N 33/0027* (2013.01); *G01N 2291/0255* (2013.01); *G01N 2291/0256* (2013.01)

(58) Field of Classification Search
CPC .. G01N 29/022; G01N 33/004; G01N 29/326; G01N 29/036; G01N 33/0027; G01N 33/0016; G01N 29/222; G01N 2291/0255; G01N 2291/0256
USPC ....................... 73/25.01, 25.05, 31.01, 31.05
See application file for complete search history.

(56) References Cited

U.S. PATENT DOCUMENTS

| | | | | |
|---|---|---|---|---|
| 5,406,829 A | * | 4/1995 | Ravel ................. | G05D 23/1928 73/24.01 |
| 2012/0028846 A1 | * | 2/2012 | Yaghi ................... | G01N 27/125 506/39 |
| 2014/0109649 A1 | * | 4/2014 | Fleischer ........... | G01N 27/4143 73/31.02 |

* cited by examiner

*Primary Examiner* — Benjamin R Schmitt
(74) *Attorney, Agent, or Firm* — Mark B. Floyd

(57) ABSTRACT

A gas sensor comprises at least one transducer and a sensing material (e.g., a metal-organic framework) disposed on the transducer. The sensing material has a temperature-dependent gas sorption behavior. A detector is arranged to detect responses of the transducer to sorption and/or desorption of a target gas in the sensing material and to output transducer measurement signals indicative of the transducer responses. At least one thermal element changes the temperature of the sensing material by heating and/or cooling, and at least one temperature sensor (which may be integral with the thermal element) is arranged to measure a temperature of the sensing material. At least one processor determines the quantity (e.g., concentration, partial pressure, or mass) of the target gas according to the temperature of the sensing material at which the transducer measurement signals satisfy a signal value condition.

22 Claims, 11 Drawing Sheets

GAS SENSOR INCORPORATING A TEMPERATURE-CONTROLLED SENSING MATERIAL

CROSS REFERENCE TO RELATED APPLICATIONS

This application claims the benefit of U.S. provisional patent application 62/553,756 filed on Sep. 1, 2017 which application is hereby incorporated by reference in its entirety.

BACKGROUND

The invention relates generally to sensors for detecting substances, and in particular to a gas sensor for monitoring the presence or quantity of a target gas in an environment or gas sample.

Chemical sensing of gases is an important technology in several fields including environmental monitoring, industrial safety, and public security. Depending on the application and target gas, different operating principles have been deployed, ranging from electrochemical, metal-oxide semiconductor, and non-dispersive infrared absorption. With the recent advancement of smartphones, wearables, and connected sensor devices, many more chemical sensing applications have emerged. In particular monitoring air quality for the health, safety and well being of consumers is receiving considerable interest. The problem is that existing technologies and sensor devices do not scale to the small size, low cost, and low power consumption that is required for these emerging applications.

One approach to a scalable gas sensor is a solid-state device based on a sensing material applied as a coating to a resonant mass transducer. This architecture can scale in size, cost, and power, but the challenge lies in the development of a sensing material that can provide sufficient sensor performance. One problem to overcome is that resonant chemical sensors can be highly sensitive to other gases including even moderate changes in relative humidity. When measuring an analyte in ambient environmental conditions, the sensor indicates not only a mass change due to the presence of a target gas, but also due to the additional adsorption of water molecules in the sensing material. While many sensing materials can be tailored to detect specific analyte molecules with low cross sensitivity, the absorption of water molecules is a more difficult problem to solve due its omnipresence and chemical activity.

Carbon dioxide ($CO_2$) sensors are currently deployed for monitoring indoor air quality to ensure adequate ventilation and as a component of demand-controlled ventilation systems. However, current optical $CO_2$ sensors are costly and prone to long-term drift, which requires manual recalibration about every six months. A low-cost sensor not requiring manual calibration would enable an expanded deployment of demand-controlled ventilation and indoor air quality $CO_2$ monitoring. Past attempts to utilize adsorbent-based sensors have failed to achieve sufficient sensitivity and immunity to interference due to variations in humidity, which cause an undesired response in the sensor device. There is still a need for a simple, low cost, sensor to detect analyte that overcomes the problems of humidity and water adsorption by the sensing material.

SUMMARY

According to an aspect, a sensor device comprises at least one transducer (e.g., a resonant mass transducer or a calorimeter). A sensing material is disposed on the transducer, and the sensing material has an ability to adsorb or absorb an amount of the target gas that depends on a temperature of the sensing material and a concentration or partial pressure of the target gas. At least one detector is arranged to detect responses of the transducer to sorption or desorption of the target gas in the sensing material and to output transducer measurement signals indicative of the responses of the transducer. At least one thermal element is arranged to change the temperature of the sensing material by heating and/or cooling, and a temperature sensor (which may be integral with the thermal element) is arranged to measure a temperature of the sensing material and to output temperature measurement signals. At least one processor or controller is in communication with the detector and the temperature sensor to receive the transducer measurement and temperature measurement signals or data. The processor is programmed to determine a quantity of the target gas according to the temperature of the sensing material at which the transducer measurement signals satisfy a signal value condition.

In some embodiments, the signal value condition is satisfied at an inflection point on a curve defined by, derived from, or fitted to the values of the transducer measurement signals. The processor may identify the inflection point on the curve according to an extremum (minimum or maximum) of a first derivative of the curve, or according to a zero-crossing of the second derivative of the curve. In some embodiments, the signal value condition is satisfied at a point on a curve defined by, derived from, or fitted to the values of the transducer measurement signals where the absolute value of the slope of the curve is greater than or equal to a threshold value, or where the absolute value of a first derivative of the curve is greater than or equal to the threshold value. In some embodiments, the signal value condition is satisfied if the transducer measurement signals indicate a step change in the amount of the target gas adsorbed or absorbed in the sensing material, with a corresponding step change in the values of the transducer measurement signals. The processor may be programmed to determine whether the step change occurs by comparing a change in the values of the transducer measurement signals to a minimum step height within a temperature range or gas concentration range that is narrower than a maximum step width. Of course, combinations of these embodiments are also possible as more than one signal value condition may be satisfied concurrently. Although these are preferred embodiments, it is not necessary for the processor to perform calculus. For example, in an alternative embodiment with a simpler processor, the signal value condition is satisfied if the values of the transducer measurement signals have a rate of change with respect to temperature or with respect to gas concentration that is greater than or equal to a threshold value, or if the rate of change is a maximum.

Because the transducer measurement signals (e.g., frequency signals for a resonant mass transducer) depend on a specific temperature-dependent sorption of the target gas in the sensing material, the transducer measurement signals are not expected to drift significantly over time or require manual calibration over the lifetime of the sensor device. This sensor device is inherently selective, i.e., interfering substances such as water vapor or volatile organic compounds (VOCs) will have only a small or negligible effect on the temperature of the sensing material at which the transducer measurement signals satisfy the signal value condition. The temperature of the sensing material at which the signal value condition is satisfied may then be used to determine the quantity (e.g., partial pressure, concentration, or mass) of the target gas with good accuracy (e.g., by calibration curves or a look-up table).

According to another aspect, a method is provided for detecting at least one target gas in an environment or sample. The method comprises changing the temperature of a sensing material disposed on at least one transducer, wherein the sensing material has an ability to adsorb or absorb an amount of the target gas that depends on a temperature of the sensing material and a concentration or partial pressure of the target gas. The method also comprises detecting responses of the transducer to sorption or desorption of the target gas in the sensing material, and outputting transducer measurement signals indicative of the responses of the transducer. At least one processor is utilized to determine a quantity of the target gas according to the temperature of the sensing material at which the transducer measurement signals satisfy a signal value condition.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. An element includes one or more elements. Any recitation of an element is understood to refer to at least one element. A plurality of elements includes at least two elements. Unless otherwise required, any described method steps need not be necessarily performed in a particular illustrated order. A first element (e.g. a signal or data) derived from a second element encompasses a first element equal to the second element, as well as a first element generated by processing the second element and optionally other signals or data. Making a determination or decision according to (or in dependence upon) a parameter encompasses making the determination or decision according to the parameter and optionally according to other signals or data. Unless otherwise specified, an indicator of some quantity/data may be the quantity/data itself, or an indicator different from the quantity/data itself such as a signal from which the quantity/data can be determined.

Transducers for detecting substances use a sensing material that adsorbs or absorbs molecules of a target gas (e.g., $CO_2$). The sorption of the gas molecules in the sensing material changes properties that are reflected in a mechanical or electromechanical response of the transducer (e.g., a frequency shift). Resonant mass transducers are sensitive to small amounts of water vapor even at moderate levels of relative humidity. When monitoring a target gas in ambient conditions, the transducer responses may indicate uptake (e.g., a mass change) in the sensing material not only due to the target gas, but also due to the additional adsorption of water molecules in the sensing material. This disclosure provides devices and methods that overcome the inaccuracy or interference in sensing target gas caused by water vapor or other interfering substances in the sensing material.

Figure 1:
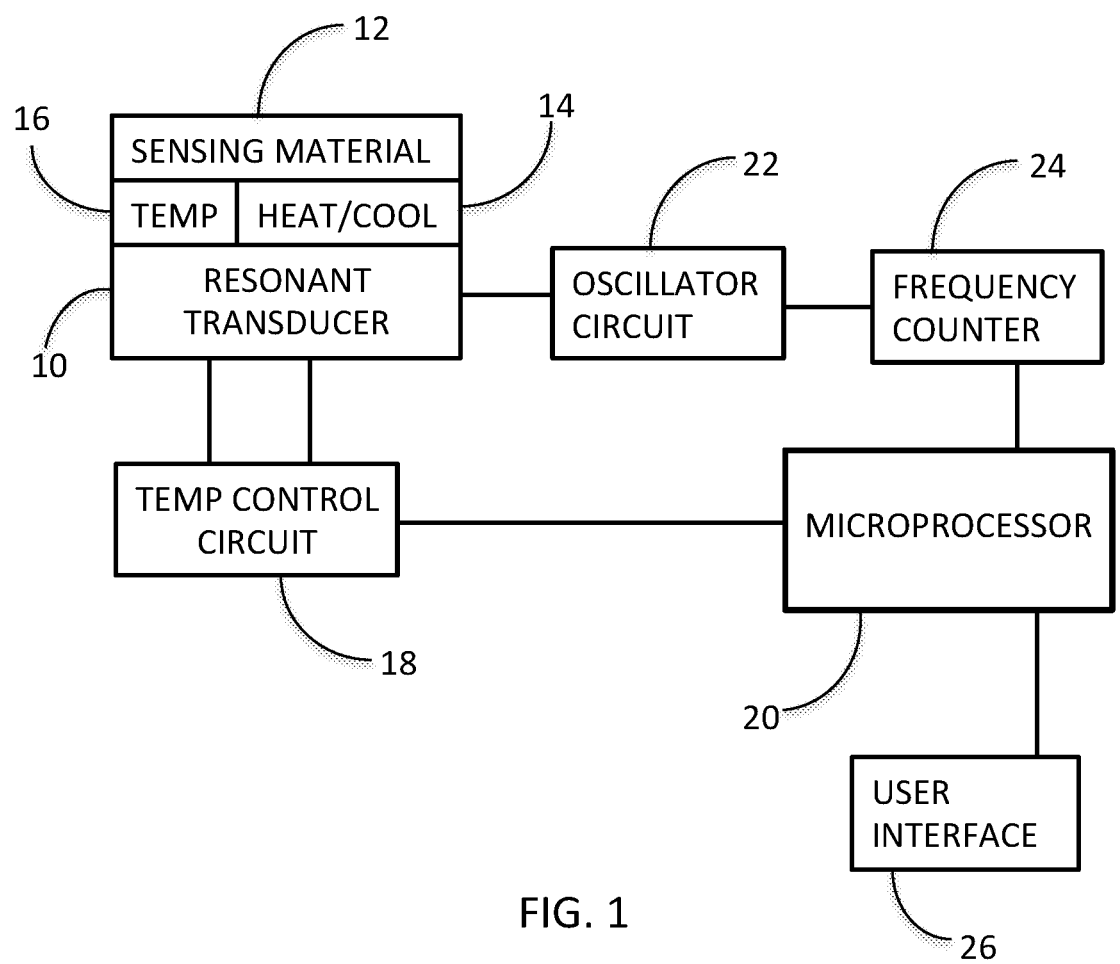
FIG. 1 is a block diagram of a sensor device according to a first embodiment of the invention.

FIG. 1 shows a schematic block diagram of a device for monitoring a target gas (e.g., $CO_2$). The device comprises a sensing material 12 that adsorbs or absorbs the target gas, if present in the environment or sample to which the device is exposed. The sensing material 12 is disposed (e.g., coated) on a transducer 10. In preferred embodiments, the transducer is a resonant mass transducer such as a quartz crystal microbalance (QCM), surface acoustic wave (SAW) transducer, cantilever or a capacitive micromachined ultrasonic transducer (CMUT), and the gas uptake (e.g., mass loading) in the sensing material 12 is monitored by a change in the transducer frequency, quality factor, stiffness, strain or a combination of these parameters. In other embodiments, many other types of transducers may be used, such as a calorimeter having the sensing material. In the calorimeter embodiment, the transducer measurement signals are indicative of heat evolved or consumed in the sensing material due to the adsorption or desorption, respectively, of the target gas.

The sensing material 12 is preferably a porous coordination polymer (PCP), and most preferably a type of PCP known as a metal-organic framework (MOF) material. In preferred embodiments, the sensing material 12 is from a family of porous metal-organic framework materials known as amine-appended $M_2(DOBPDC)$. Such materials exhibit characteristic gas uptake behavior that varies with temperature and the concentration of the target gas (e.g., $CO_2$). In particular, the material mmen-$Mg_2$(DOBPDC) exhibits an impressive 14 weight percent $CO_2$ uptake with a sharp mass uptake step that depends on temperature and the concentration of $CO_2$.

Figure 2A:
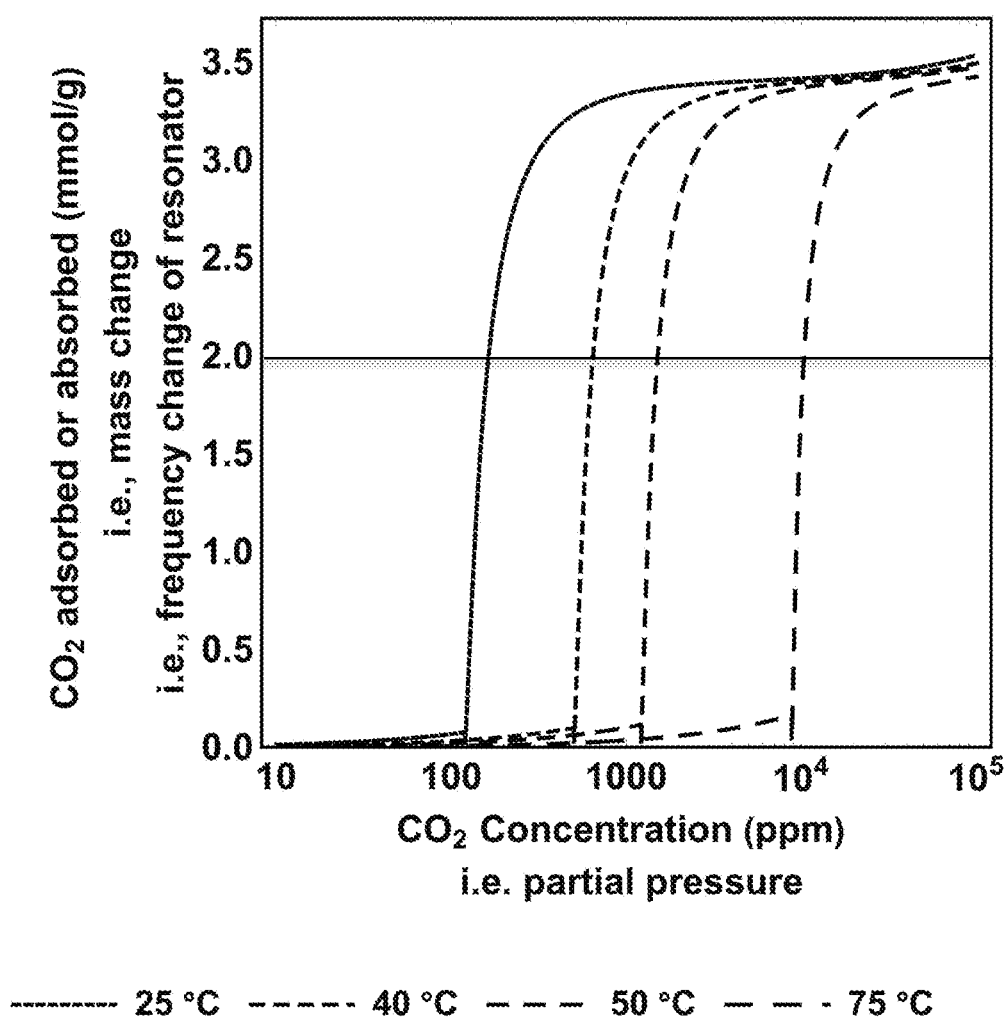
FIG. 2A is a graph illustrating uptake or sorption of carbon dioxide in a metal-organic framework (MOF) vs. concentration of the carbon dioxide the environment, with four isotherm curves at four different temperatures.

FIG. 2A is a graph illustrating sorption of $CO_2$ in a MOF (DOBPDC) vs. concentration (i.e., partial pressure) of the $CO_2$ in the environment or gas sample to which the MOF is exposed. Pressure here refers to the partial pressure of a gas, not ambient or atmospheric pressure. Partial pressure as used herein is interchangeable (synonymous) with the gas concentration. These "isotherm" curves at four different temperatures are plotted (25° C., 40° C., 50° C. and 75° C.). Each isotherm represents sorption of the target gas at a different temperature. Each curve has a sharp "step" change or transition (i.e. the steep part of the curve) that indicates an abrupt or sharp change (increase or decrease) in the amount of the target gas adsorbed or absorbed in the MOF sensing material. Step change means an abrupt or sharp change (increase or decrease), not a gradual change. This step change in the mass or heat of $CO_2$ adsorbed occurs at a different concentration for each temperature of the sensing material, so that by finding the temperature of the sensing material at which a step change in the amount of the target gas in the sensing material occurs (indicated by a corresponding step change in transducer measurement signal values, such as frequency), we can determine the concentration of the target gas in the environment or sample to which the sensor device is exposed.

Figure 2B:
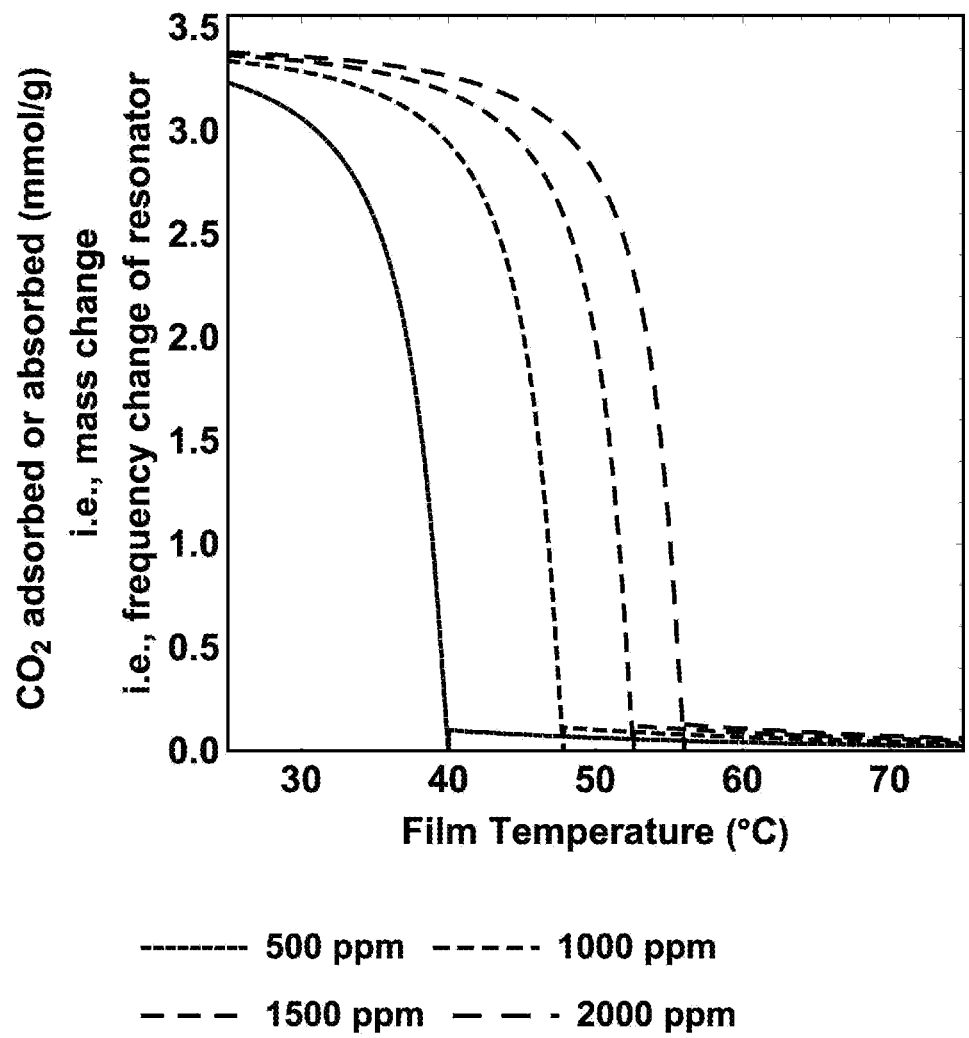
FIG. 2B is a graph illustrating sorption or uptake of carbon dioxide in the film of MOF sensing material vs. Temperature of the film of MOF sensing material, with four isobar curves at four different partial pressures (i.e. gas concentrations).

FIG. 2B is a graph illustrating sorption (gas uptake in mmol/g) of carbon dioxide in the film of MOF sensing material vs. temperature of the film of MOF sensing material, with four "isobar" curves at four different partial pressures (i.e. gas concentrations). These isobar curves at four different concentrations are plotted (500 ppm, 1000 ppm, 1500 ppm and 2000 ppm). Each isobaric curve represents sorption of the target gas at a different concentration, and each curve has a sharp "step" change or transition (i.e. the steep part of the curve) that corresponds to an abrupt or sharp change (increase or decrease) in the amount of the target gas adsorbed or absorbed in the MOF sensing material. This step change in sorption of $CO_2$ occurs at a different temperature of the MOF sensing material for each concentration, so that by finding the temperature of the sensing material at which a step change in the amount of the target gas in the sensing material occurs (indicated by a corresponding step change in transducer measurement signal values, such as frequency), we can determine the concentration of the target gas in the environment or sample.

Referring again to FIG. 1, at least one thermal element 14 is positioned to heat or cool the transducer 10 and the sensing material 12. The sensing material 12 may require heating or cooling to reach the transition temperature at which there is a step change in target gas adsorbed in the sensing material 12. The step change in mass (rapid increase or decrease) is detected by monitoring the transducer measurement signals (e.g., sharp increase or decrease in frequency). The sensing material 12 may require heating or cooling depending upon the ambient temperature of the sensor environment and if the transition temperature (based on the concentration of $CO_2$ in the environment) is higher or lower than the ambient temperature.

The term "thermal element" means at least one heater, cooling element, or device that provides both heating and cooling. For example, in some embodiments, the thermal element is simply a resistive heater, and passive cooling is used. In other embodiments, the thermal element is an active cooling element. In still other embodiments, the thermal element provides both active heating and cooling, in which case the thermal element 14 is preferably a thermoelectric device (TED) that heats and cools the sensing material 12. In general, suitable heating elements include conductive heaters, convection heaters, or radiation heaters. Examples of conductive heaters include resistive or inductive heating elements, e.g., resistors or thermoelectric devices. Convection heaters include forced air heaters or fluid heat-exchangers. Suitable radiation heaters include infrared or microwave heaters. Similarly, various cooling elements may be used to cool the sensing material 12. For example, various convection cooling elements may be employed such as a fan, Peltier device, refrigeration device, or jet nozzle for flowing cooling fluids. Alternatively, various conductive cooling elements may be used, such as a heat sink, e.g. a cooled metal block.

A temperature sensor 16 is arranged to measure a temperature of the sensing material 12. In some embodiments, the temperature sensor 16 is integral with the thermal element 14, for example there are some heaters (e.g., resistive heaters) that also perform temperature sensing by measuring an electric property of the heater circuit, as is known in the art. Alternatively, the temperature sensor 16 may be a separate element from the thermal element 14, e.g., the temperature sensor 16 may be a thermistor. A temperature control circuit 18 is connected to the thermal element 14 and a microprocessor 20. The temperature control circuit 18 preferably operates under microprocessor control to heat and/or cool the sensing material 12. The position of the thermal element 14 and temperature sensor 16 (which may be integral with the thermal element 14 in some embodiments) with respect to the transducer 10 and the sensing material 12 may be different for different embodiments and applications of the sensor device. For example, FIG. 1 shows an embodiment in which the thermal element 14 and the temperature sensor 16 are positioned between the sensing material 12 and the resonant transducer 10.

Figure 3:
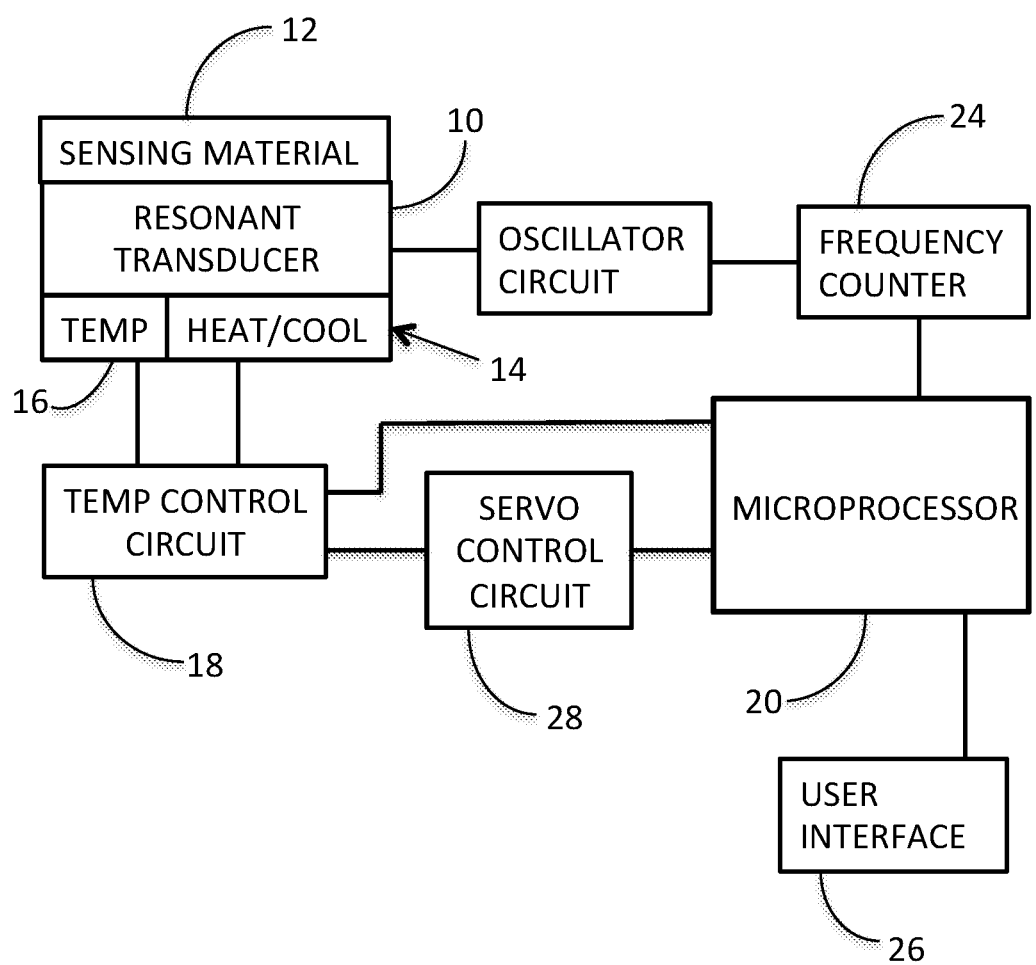
FIG. 3 is a block diagram of a sensor device according to another embodiment of the invention.

FIG. 3 shows another embodiment in which the thermal element 14 and the temperature sensor 16 are positioned on the backside of the resonant transducer 10 (e.g., a QCM), with the sensing material 12 disposed (e.g., coated, deposited or grown) on the topside of the transducer 10. This is a convenient arrangement of parts when the transducer is a QCM having topside and backside electrodes positioned on opposing sides of a quartz substrate. The thermal element 14 and temperature sensor 16 are preferably a resistive heater and a thermistor positioned on the backside of the QCM, and the sensing material 12 (e.g., a MOF) is positioned on the topside of the QCM (e.g., disposed over the top electrode of the QCM). In many embodiments such as this, the action of heating/cooling the transducer 10 and measuring the temperature of the transducer 10 is sufficient to also heat/cool the sensing material 12 and measure the temperature of the sensing material 12, since the sensing material 12 will be at the same temperature as the transducer 10. It is not necessary to have direct physical contact between the sensing material 12, the thermal element 14 and the temperature sensor 16. So long as there is adequate thermal contact between these elements of the device, the temperature sensor 16 positioned on the backside of the transducer 10 will be at nominally the same temperature as the sensing material 12, and heat will be able to flow from the thermal element 14 through the transducer 10 to the sensing material 12.

Referring again to FIG. 1, the device also includes at least one detector (e.g., a readout circuit for a resonant mass transducer) arranged to detect responses of the transducer 10 when substances (e.g., molecules of the target gas and/or water molecules) are adsorbed or absorbed in the sensing material 12. The readout circuit outputs transducer measurement signals indicative of the transducer responses. In a preferred embodiment, the transducer is a resonant mass transducer (e.g., a QCM), the transducer responses to mass changes in the sensing material 12 are frequency shifts, and the detector is a readout circuit comprising an oscillator circuit 22 that drives the transducer 10 and a frequency counter 24 that measures the frequency (e.g., resonance frequency or frequency shifts). Many suitable oscillator circuits and frequency counters are known in the art. The oscillator circuit 22 and the frequency counter 24 output the transducer measurement signals (e.g., frequency signals from the frequency counter 24) to the microprocessor 20.

Although a QCM is the presently preferred transducer, the oscillator circuit 22 and the frequency counter 24 are the preferred detector, and frequency signals are the presently preferred "transducer measurement signals", there are many other suitable transducers, detection mechanisms for those transducers, and transducer measurement signals output from those detectors that are known in the art. Transducer responses that may be detected and output as transducer measurement signals include a change in frequency, resonance frequency, dissipation, quality factor, stiffness, or strain. The responses of the resonant transducer to mass loading in the sensing material are often detected using an electrical property, such as a change in impedance of the circuit driving an oscillating motion of the transducer 10.

Many electrical detection methods are known in the art to detect transducer responses to a change in uptake (i.e., sorption and desorption) of the target gas in the sensing material for a resonant mass transducer, or an array of transducers, and to output transducer measurement signals indicative of the transducer responses. In some embodiments, an optical detector is used to detect deflection or frequency shifts of the transducer 10. In other embodiments, the transducer 10 is an electronic element such as a resistor or a capacitor, and the sorption of mass in the sensing material 12 is monitored by a change in the transducer device resistivity, capacitance, or other electrical property. Many other types of transducers may be employed, such as heat-measuring transducers (e.g. a calorimeter).

The microprocessor 20 receives the transducer measurement signals and the temperature measurement signals. The microprocessor 20 is programmed to determine a quantity of the target gas according to the temperature of the sensing material at which the transducer measurement signals satisfy a signal value condition (e.g., determining gas concentration using look-up tables or calibration curves stored in memory of the microprocessor that relate temperature of the sensing material at which a sharp or steep change in gas sorption or desorption occurs to concentration of the target gas in the environment or sample). A user interface 26 is preferably connected to the processor 20. The user interface 26 preferably includes a display for displaying a quantity of the target gas (e.g., concentration, mass or partial pressure), speakers or other mechanisms for sounding an alarm at certain gas concentrations, and at least one user-input device for selecting parameter values, such as a target concentration of the gas at which an alarm should be initiated.

Figure 6:
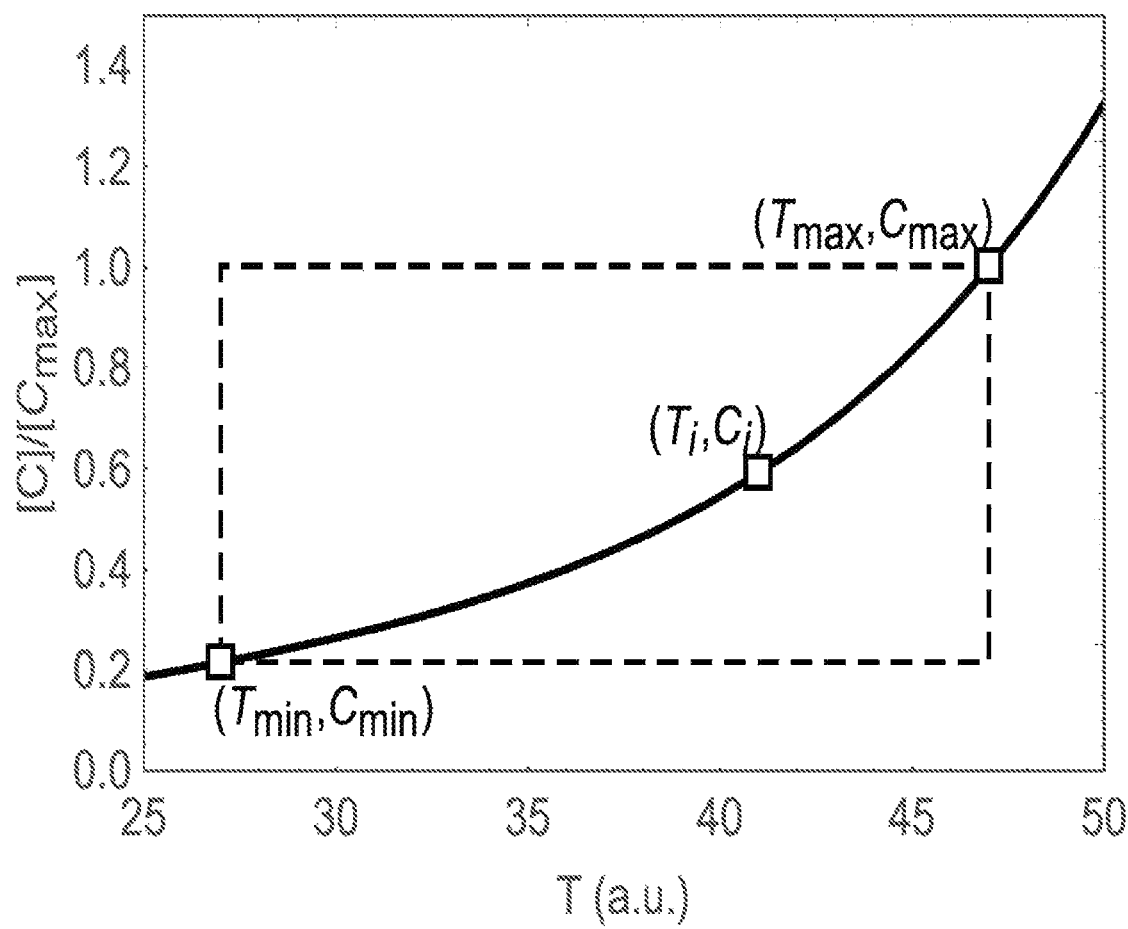
FIG. 6 is a calibration curve of concentration versus temperature, according to some embodiments of the invention, with dashed lines of a rectangle indicating ranges of the sensor in concentration and temperature.

In a first simple example of operation, the sensing material 12 is heated by the thermal element 14 from room temperature (e.g., 25° C.) to a pre-determined maximum temperature (e.g., 75° C.). The temperature of the sensing material 12 at which the transducer measurement signals satisfy a signal value condition (e.g., the temperature at which there is a step change in the sorption or desorption of $CO_2$ as determined from the change in transducer measurement signal values) is determined by the processor. The temperature at which the step change occurs is used to determine the concentration of $CO_2$ with good accuracy (e.g., by calibration curves or a look-up table stored in the memory of the microprocessor 20). FIG. 6 shows an example of a calibration curve and is discussed below. For example, referring again to FIGS. 2A and 2B, if there is a large change (increase or decrease) in frequency at 40° C., corresponding to a step change in gas uptake, then the $CO_2$ concentration is determined as approximately 820 ppm. Or if there is a large change (increase or decrease) in frequency at 50° C., corresponding to a step change in gas uptake, then the $CO_2$ concentration is determined as approximately 1200 ppm.

Because the transducer measurement signals (e.g., frequency signals for a resonant mass transducer) depend on a specific temperature-dependent sorption of the target gas in the sensing material, the transducer measurement signals do not drift significantly over time and do not require manual calibration over the lifetime of the sensor device (e.g., 10 years). This sensor device is inherently selective, i.e., interfering substances such as water vapor or volatile organic compounds (VOCs) will have only a small or negligible effect on the temperature of the sensing material at which the transducer measurement signals satisfy the signal value condition (e.g., the temperature of the sensing material 12 at which the signal value curve has a step change or an inflection point). The temperature of the sensing material 12 at which the signal value condition is satisfied may then be used to determine the quantity (e.g., partial pressure, concentration, or mass) of the target gas with good accuracy.

Figure 4:
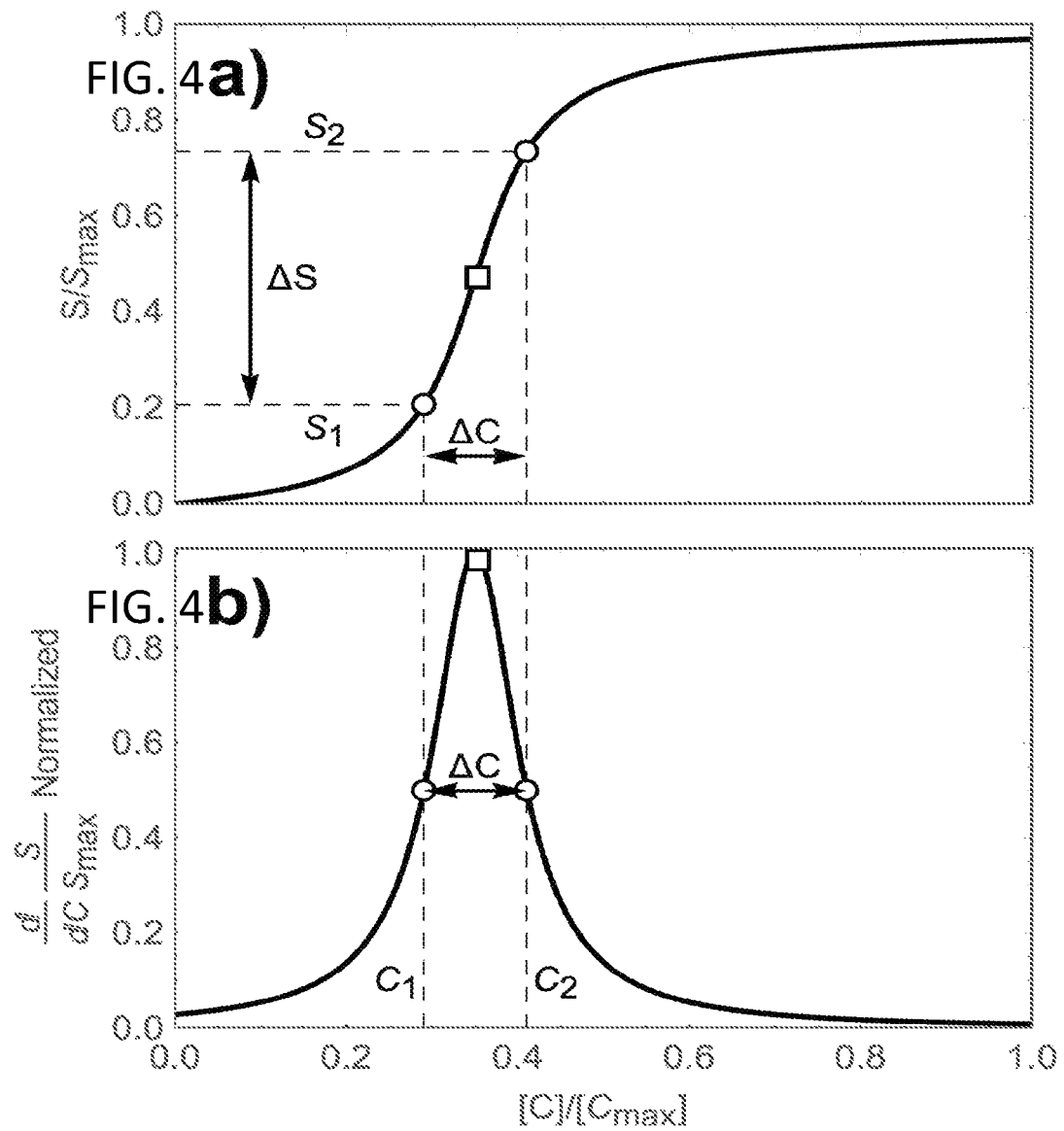
FIG. 4A is a graph illustrating signal value vs. concentration of a target gas for an isotherm curve having a step change in signal values and an inflection point according to some embodiments of the invention.
FIG. 4B is a graph illustrating a first derivative of the curve in FIG. 4A.

FIG. 4A and FIG. 4B show an isotherm of a MOF sensing material. FIG. 4A is a graph illustrating signal value vs. concentration of a target gas for an isotherm curve having a step change in signal values. FIG. 4B shows a first derivative of the signal value curve of FIG. 4A. The term "signal value curve" is intended to mean a curve defined by, derived from, or fitted to the values of the transducer measurement signals. The curve may be defined by the signal values by plotting the signal values vs. temperature or concentration as in FIGS. 4A and 4B. Or the signal value curves may be derived from the signal values, like FIGS. 2A and 2B that plot gas uptake (mmol/g) vs. concentration or temperature, respectively. The uptake is proportional or sometimes inversely proportional to the signal values. Alternatively, one skilled in the art will recognize that a curve may be fitted to the signal values vs. temperature or concentration using any number of curve fitting algorithms.

An isotherm with a step change in uptake and an inflection point is plotted in FIG. 4A. The vertical axis, representing the transducer measurement signal S, has been normalized to the maximum signal, $S_{max}$, the signal corresponding to the maximum concentration to be measured, $C_{max}$. The horizontal axis represents target gas concentration C, normalized to the maximum concentration to be measured, $C_{max}$. It is not necessary to normalize in alternative embodiments, and normalization is an optional preferred technique.

The "step" change may be characterized by a step height $\Delta S$ and a step width $\Delta C$. In some embodiments, the step width $\Delta C$ may be defined by first computing the derivative, $d/dC(S/S_{max})$ and finding the full width at half maximum (FWHM) of the resulting peak as shown in FIG. 4B. The points on the curve at the half-maximum define two concentrations, $C_1$ and $C_2$. In the event that $C_1$ occurs at a nonphysical negative concentration, $C_1$ is taken to be zero.

Accordingly, the step width may be defined as, $\Delta C = C_2 - C_1$. One can define the step height $\Delta S$ by first finding the concentrations $C_2$ and $C_1$ and their corresponding heights on the isotherm, signal values $S_2$ and $S_1$. The difference in height of these two points gives the step height, defined as $\Delta S = S_2 - S_1$. An advantage of the sensor device is that it achieves a very large change in signal $\Delta S$ for a very small concentration of the target gas, so that one may confidently calculate the concentration.

Mathematically, a maximum (peak) in the first derivative of FIG. 4B corresponds to an inflection point in FIG. 4A, which also corresponds to a zero-crossing point of the second derivative of the curve. As used herein, both inflection points and undulation points are called inflection points. The square-shaped symbol on the curves at the inflection point in FIG. 4A and at the peak of the derivative in FIG. 4B indicates the concentration C about which the step change is centered. The step height $\Delta S$ should be sufficiently tall and the step width $\Delta C$ should be sufficiently narrow to indicate when a step change in the amount of target gas adsorbed in the sensing material has occurred. In a preferred embodiment, the step height $\Delta S > 0.25 * S_{range}$, where the signal range of the sensor device $S_{range} = S_{max} - S_{min}$. The signal value $S_{max}$ is the signal value at the upper limit of the sensor range, and the signal value $S_{min}$ is the signal value at the lower limit of the sensor range. Also in a preferred embodiment, the step width $\Delta C < 0.1 * C_{range}$, where $C_{range} = C_{max} - C_{min}$.

As a working example of a $CO_2$ sensor, the MOF material amine-appended $M_2$(DOBPDC) is disposed on a quartz resonator and the resulting resonant frequency is 150 MHz. The concentration range of the sensor $C_{range} = C_{max}$ to $C_{min} = 400$ ppm to 2000 ppm. The measured frequency at 400 ppm $CO_2$ and a constant temperature is 146 MHz, while at 2000 ppm $CO_2$ and the same temperature, the measured frequency is 130 MHz.

The concentration range $C_{range} = C_{max} - C_{min} = 2{,}000$ ppm–400 ppm$=1{,}600$ ppm.

The signal range $S_{range} = S_{max} - S_{min} = 146$ MHz–130 MHz$=16$ MHz

The step width $\Delta C < 0.1 * C_{range} = 0.1 * 1{,}600$ ppm$=160$ ppm

The step height $\Delta S > 0.25 * S_{range} = 0.25 * 16$ MHz$=4$ MHz

Thus, in this example, a "step" change is identified by the microprocessor when: the change in signal or "step" height $\Delta S > 4$ MHz, and the step width $\Delta C < 160$ ppm.

A step change may also be characterized by a step height $\Delta S$ and a step width $\Delta T$, where $\Delta T$ is the change in temperature or the temperature range over which the change in signal values occurs to qualify as a "step" change. The minimum step height $\Delta S$ should be sufficiently tall and the maximum step width $\Delta T$ should be sufficiently narrow (e.g., a maximum step width $\Delta T$ of 10° C., more preferably 5° C., and most preferably about 2° C.) to indicate when a step change in the amount of target gas adsorbed in the sensing material has occurred, as opposed to a gradual change. In some embodiments in which the temperature of the sensing material is held steady at a setpoint temperature, such as a concentration alarm embodiment described below, it is useful to define a maximum step width $\Delta C$ in terms of a concentration range, or to take a derivative of the signal value curve with respect to concentration, because there is no change in temperature when it is held at a setpoint. In other embodiments, the temperature is changed either by varying (e.g., sweeping or oscillating) the temperature over a temperature range or by a servomechanism, and it is useful to define a maximum step width $\Delta T$ in terms of a temperature range, or to take a derivative of the signal value curve with respect to temperature.

To identify a step change in gas uptake, the microprocessor may compare the transducer measurement signal values to at least one threshold value (e.g., determine if one or more of the signal values, or the absolute value of a change in signal values, meets or exceeds a threshold value). The threshold value is preferably greater than or equal to 25% of the signal range $S_{range}$, where $S_{range} = S_{max} - S_{min}$. For example, if the signal range is $S_{range} = S_{max} - S_{min} = 20$ MHz, then the threshold value is set to at least 5 MHz for the increase/decrease in frequency. In some embodiments, a threshold value of 50% to 70% of the signal range $S_{range}$ is used, or for a very steep "step" change, a threshold value of 70% to 90% of the signal range $S_{range}$ may be used.

In some embodiments, the gas concentration is determined according to the temperature of the sensing material at an inflection point (indicated by the square-shaped symbols on FIGS. 4A and 4B) of a signal value curve. The processor may identify the inflection point on the curve according to an extremum (minimum or maximum) of a first derivative of the curve. In embodiments in which the temperature is held at a setpoint temperature, it may be useful to take the derivative of signal value with respect to concentration, as in FIG. 4B. In other embodiments in which the temperature of the sensing material is changed, it is useful to take the derivative of the signal value curve with respect to temperature, and the inflection point may be identified as a minimum of the first derivative (e.g., taking a first derivative of the curve of FIG. 2B).

Although it is presently preferred to determine gas concentration from the temperature at an inflection point, the scope of the invention is not limited to this embodiment. In some embodiments, it is sufficient to just identify the temperature of the sensing material at a steep part of the signal value curve, not necessarily an inflection point, indicating a sharp increase or decrease in gas sorption in the sensing material. For example, the signal value condition may be satisfied at a point on a signal value curve where the absolute value of the slope of the curve is greater than or equal to a threshold value, or a mathematical equivalent where the absolute value of a first derivative of the curve is greater than or equal to the threshold value. Preferably, for any particular choice of sensing material and target gas, the slope threshold value is selected to be within 10 to 25% of the maximum slope value (e.g., at an inflection point) for the temperature-dependent gas sorption behavior of that particular sensing material for that selected target gas to identify the temperature of the sensing material at which a sharp change in sorption occurs.

Although some embodiments utilize calculus, it is not necessary for the processor to perform calculus. In an alternative embodiment with a simpler processor, the signal value condition is satisfied if the transducer measurement signals values have a rate of change with respect to temperature or with respect to gas concentration that is greater than or equal to a threshold value, or if the rate of change is a maximum (similar to an inflection point). The threshold value for the rate of change of the transducer measurement signal values should be set to identify the sharp change in gas uptake that depends on the temperature of the sensing material and the gas concentration. For example the threshold value may be the rate at which: a change in signal values of at least 25%, and more preferably at least 50%, of the signal range of the device occurs within a narrower range of temperature or concentration (e.g., less than or equal to 10% of the total concentration range or temperature range of the sensor device). The actual threshold value selected for rate of change of the signal values with respect to concentration or temperature depends upon the specific choice of sensing material (preferably a MOF) and the selected target gas. For any particular choice of sensing material and target gas, the threshold value for rate change is preferably selected to be within 10 to 25% of the maximum rate change (similar to an inflection point) for the temperature-dependent gas sorption behavior of that particular sensing material for that selected target gas to identify the temperature of the sensing material at which a sharp change in sorption occurs.

Figure 5:
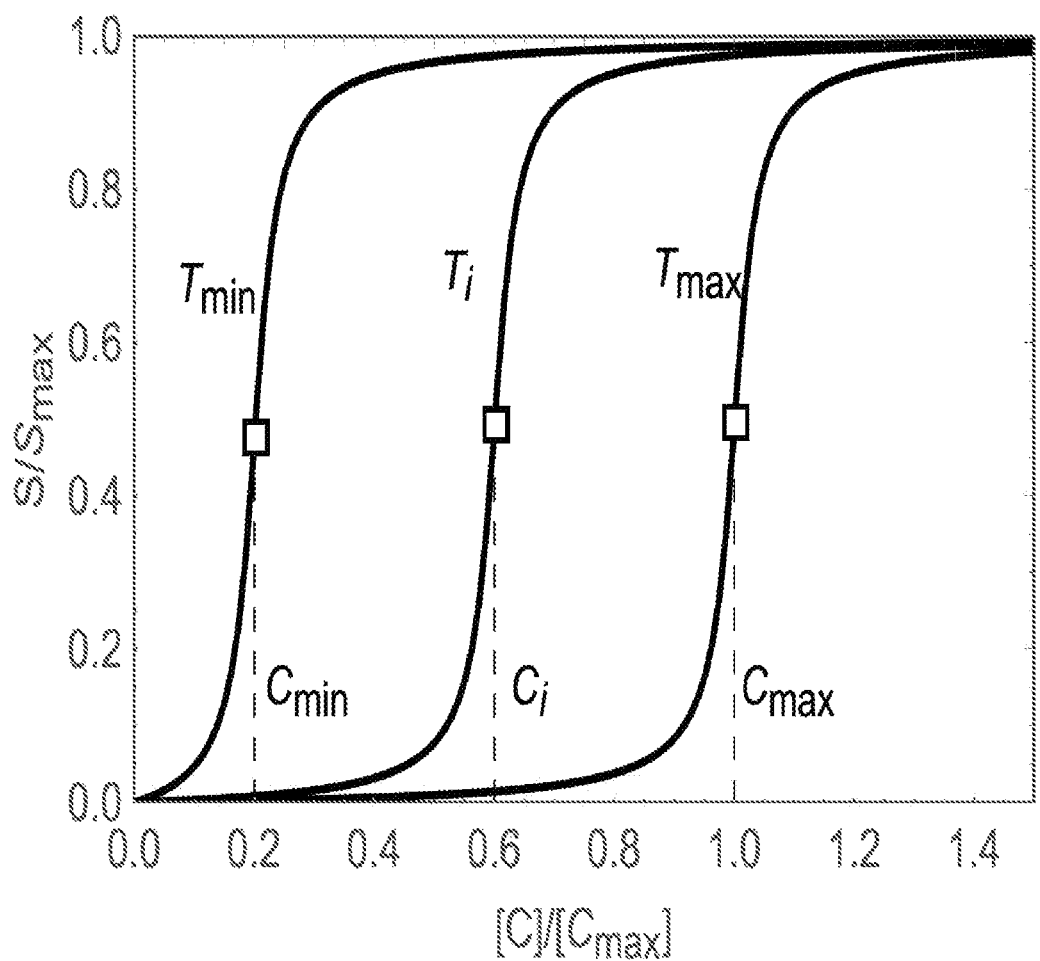
FIG. 5 is a graph of signal value vs. concentration of a target gas illustrating three isotherm curves at three different temperatures.

FIG. 5 shows isotherms of the MOF sensing material at three different temperatures. $T_{max}$ corresponds to the temperature at which the isotherm "step" change or inflection point is at the upper limit of the sensor range ($C_{max}$), and $T_{min}$ corresponds to the temperature at which the isotherm "step" change or inflection point is at the lower limit of the sensor range ($C_{min}$). The position of the step change in signal, as indicated by square-shaped symbols at the inflection points, should be tunable via a parameter (e.g. temperature) in order for the sensor device to track the target gas concentration across a range, $C_{range}=C_{max}-C_{min}$, that is larger than the step width $\Delta C$. The minimum detectable concentration, $C_{min}$, occurs at the lowest temperature, $T_{min}$. Similarly, the maximum detectable concentration, $C_{max}$, occurs at the maximum temperature, $T_{max}$. An intermediate concentration, $C_i$, is detected when the step is observed to occur at an intermediate temperature, $T_i$. The tuning range of temperatures, $T_{range}=T_{max}-T_{min}$, is preferably larger than 2° C. In many embodiments, the temperature range $T_{range}$ may be larger, e.g., 15° C. to 75° C. A preferred minimum value for the temperature range is $T_{range}>10*\delta T_{resolution}$, where $\delta T_{resolution}$=the resolution of the temperature control system. Preferably, the resolution of the temperature control system is less than 1° C., and more preferably the resolution is less than or equal to 0.1° C. for more precise temperature control and measurements.

FIG. 6 shows an example of a calibration curve. Concentration of the target gas may be calculated from a calibration curve of concentration versus temperature (e.g. the measured temperature $T_i$,) at the moment when the signal value condition is satisfied (e.g., at an inflection point or step change) as determined by the microprocessor from the transducer measurement signals S. Alternatively, a look-up table may be utilized (e.g., stored in the memory of the microprocessor) to determine the concentration by the measured temperature of the sensing material at which the signal value condition is satisfied. In some embodiments, a calibration curve may be utilized for which the data points are fit to a Taylor series using terms in even powers of T only so as to determine the slope locally.

According to another example of operation, the sensor device is operated as an alarm device that communicates an alarm when a target concentration of gas in the environment is detected. Thus, the quantity to be determined by the processor is a target concentration of the gas for the alarm signal. The processor is programmed to determine a setpoint temperature for the sensing material corresponding to the target concentration of the gas, to initiate heating or cooling of the sensing material to the setpoint temperature, and to initiate an alarm signal if the signal value condition is satisfied at the setpoint temperature. For example, approximating between the curves of FIGS. 2A and 2B, a step change (centered at an inflection point) in gas uptake at 50° C. corresponds to a concentration of approximately 1,200 ppm.

So if a user wants the sensor device to communicate an alarm when the concentration of target gas reaches 1,200 ppm, the microprocessor is programmed to determine from this target concentration a corresponding setpoint temperature, to initiate heating and/or cooling of the sensing material to a corresponding setpoint temperature (e.g., 50° C.) and to monitor the transducer measurement signals (e.g., frequency signals) corresponding to uptake. As the concentration of $CO_2$ slowly increases in the environment, there will be little change in frequency. This is the flat part of the sorption curve before the sharp transition or "step" change in gas uptake or desorption in the sensing material. If and when the concentration of target gas in the environment reaches 1,200 ppm, the uptake of the target gas in the sensing material increases or decreases rapidly in a "step" change (or at an inflection point, or both), and the transducer measurement signal values experience a corresponding sharp change (increase or decrease). The absolute value of the change in transducer measurement signal values exceeds a threshold value (e.g., $0.25*S_{range}$), indicating the step change in gas adsorbed at the target concentration of 1,200 ppm and temperature of 50° C., and the processor initiates an alarm signal.

Referring again to FIG. 1, there is a user interface 26 through which the alarm may be communicated (e.g., sound or text display). Alternatively, the microprocessor 20 may include program instructions to alert another device or external computer that there is an alarm at a target concentration. For example, an alarm signal is set that can be communicated to another system such as a building ventilation control system. Note that in this mode, the sensor device is simply an "on/off" alarm that determines if the target gas is present at a target concentration. The target concentration for an alarm should be user-selectable by inputting through the user interface 26 a desired alarm concentration that is the target concentration (e.g., 10,000 ppm) that the microprocessor 20 converts to the corresponding setpoint temperature (e.g., 75° C.) at which there is a step change (or inflection point) in signal values if the target concentration is present. The sensing material has a temperature-dependent gas sorption behavior so that the signal value condition is satisfied at the setpoint temperature only if the target gas is present at the target concentration. One skilled in the art will recognize that the target concentration for the alarm signal may be selected in a variety of ways, such as factory settings or from another device or computer system communicating with the sensor device.

FIG. 3 shows a sensor device for continuous monitoring of a target gas (e.g., $CO_2$) according to another embodiment. The device includes the additional feature of a temperature control feedback loop, such as a servo control circuit 28. Many different temperature control feedback loops are known in the art. In this embodiment, the gas concentration is continuously monitored as follows: Set the temperature of the sensing material 12 such that the frequency of the transducer 10 is in the mid-range (the horizontal line at "2" in FIG. 2A). The transducer frequency signals preferably correspond to inflection points on the signal value curves. For example, if the concentration is 10,000 ppm, then the temperature is set to 75° C. so that the transducer frequency is in the mid-range corresponding to a gas uptake of 2 mmol/g. Next, as the gas concentration in the environment changes, the temperature control feedback loop (e.g., servo via phase locked loop) adjusts the temperature of the sensing material according to the detected frequency such that the frequency of the transducer is maintained substantially around a setpoint operating frequency. For example, if the concentration of target gas decreases from 10,000 ppm to 820 ppm, in order to maintain the frequency at "2" (corresponding to a target gas uptake of 2 mmol/g), the temperature is decreased to 40° C. By mapping temperature to concentration (e.g., by calibration curves or a look-up table stored in the memory of the microprocessor) the sensor device can monitor concentration of the target gas.

Figure 7:
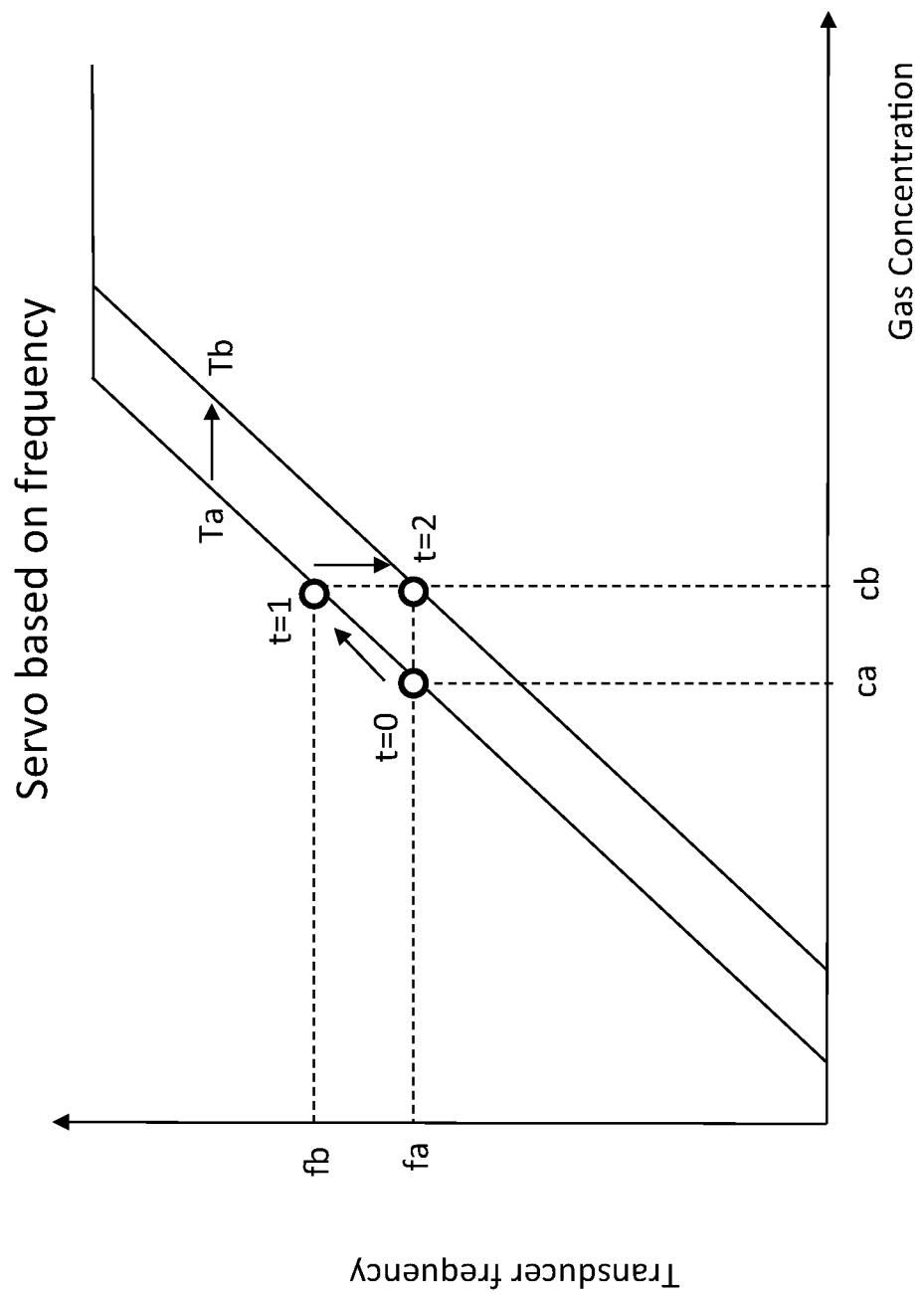
FIG. 7 is a graph of 1/(transducer frequency) vs. gas concentration, where the frequency of the transducer is maintained around a setpoint frequency, according to some embodiments of the invention.

FIG. 7 shows a graph of 1/(transducer frequency) versus gas concentration where the frequency of the transducer is maintained around a setpoint frequency $f_a$. Two "isotherm" curves at two different temperatures $T_a$ and $T_b$ are plotted. Table 2 illustrates values for time, concentration, frequency, and temperature. From time t=0 to time t=1, the gas concentration in the environment increases from concentration $c_a$ to $c_b$, thus changing the 1/frequency measurement from $f_a$ to $f_b$. To return the transducer to the setpoint frequency $f_a$, the temperature of the sensing material is changed to $T_b$ at time t=2.

TABLE 1

| Time | concentration | frequency | temperature |
| --- | --- | --- | --- |
| t = 0 | $c_a$ | $f_a$ | $T_a$ |
| t = 1 | $c_b$ | $f_b$ | $T_a$ |
| t = 2 | $c_b$ | $f_a$ | $T_b$ |

Figure 8:
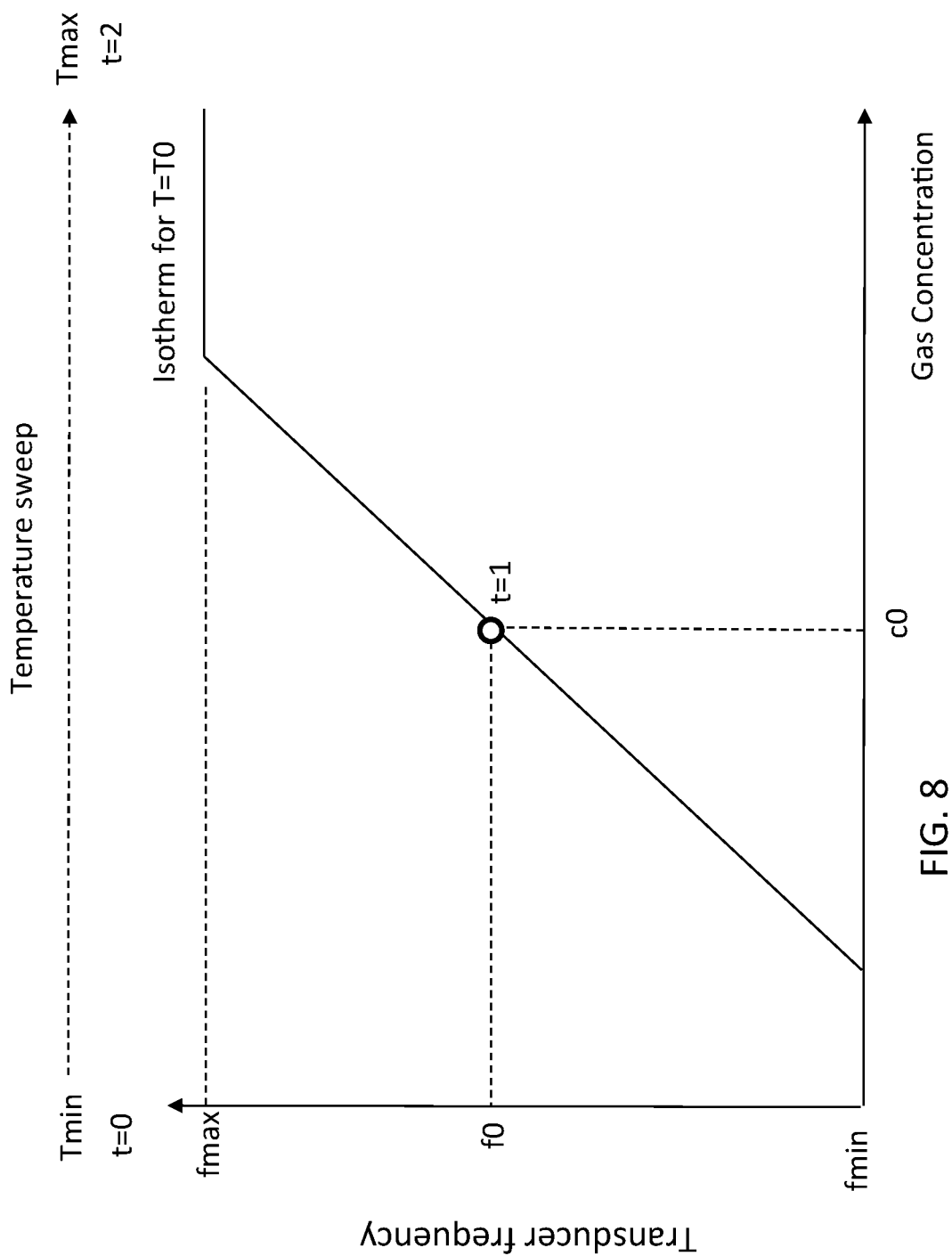
FIG. 8 is a graph of 1/(transducer frequency) versus gas concentration, where the temperature of the sensing material is swept over a temperature range, according to some embodiments of the invention.

FIG. 8 is a graph of 1/(transducer frequency) versus gas concentration, illustrating an example of varying (e.g., sweeping) the temperature of the sensing material over a temperature range $T_{min}$ to $T_{max}$. According to this example of operation, the temperature of the sensing material is swept over a temperature range to locate the sharp change in transducer measurement signals, corresponding to an inflection point or a step change in gas uptake. The temperature sweeps may be linear like a saw tooth, sinusoidal, or some other function. The temperature range of the sweeps (peak to peak) may be set to the range of the sensor device. An "isotherm" curve at temperature $T_o$ is plotted. Table 2 illustrates values for time, concentration, frequency, and temperature. As the temperature of the sensing material is increased from $T_{min}$ to $T_{max}$, at time t=1 we find the transition temperature $T_o$ at which an inflection point or a step change in uptake of the target gas occurs. We can determine the concentration $c_o$ of the target gas in the environment or sample according to the transition temperature $T_o$ at which the step change occurs (e.g., from a calibration curve or look-up table).

TABLE 2

| Time | concentration | frequency | temperature |
| --- | --- | --- | --- |
| t = 0 | $c_o$ | $f_{min}$ | $T_{min}$ |
| t = 1 | $c_o$ | $f_o$ | $T_o$ |
| t = 2 | $c_o$ | $f_{max}$ | $T_{max}$ |

According to another example of operation, the temperature variations (e.g., sweeps or oscillations) may be "smarter" than simply sweeping the temperature through the entire temperature range of the sensor device. Instead, the smarter temperature variations may have a smaller amplitude and a center temperature that moves up and down depending on the concentration changes. For example, the temperature range may have a smaller amplitude (e.g., 5° C.) and oscillate around a center temperature that tracks the gas concentration so that the temperature of the sensing material is always near the temperature at which there is an inflection point on the signal value curve. In this case, the center temperature of the swept range may be selected according to the last known concentration of the target gas determined by the sensor device or according to a target concentration.

Self-calibration of the sensor device is an important advantage. One may use the user interface 26 to initiate a calibration procedure, or initiation of the calibration procedure may be automatically programmed in the microprocessor 20. To calibrate, we look for an inflection point or a step change in transducer measurement signals (e.g., frequency) as we change the temperature of the sensing material 12. For example, approximating between the curves shown in FIGS. 2A and 2B, if the sensing material is heated from room temperature (e.g., 25° C.) and there is a "step" change in transducer frequency at 40° C., then the $CO_2$ concentration is determined to be about 820 ppm. Whereas if there is a large "step" change in transducer frequency at 50° C., then the $CO_2$ concentration is determined to be approximately 1200 ppm. The temperature can be oscillated around a step for a period of time to improve the precision of the calibration. The sensor device may also be used as a calibration device to calibrate other devices because of the improved accuracy of the concentration readings that depend upon temperature and concentration, not interference from humidity or VOCs.

The above description illustrates embodiments of the invention by way of example and not necessarily by way of limitation. Many other embodiments are possible. For example, only one sensor element was shown at a time for simplicity of understanding in the patent drawings, but arrays of sensor devices are also possible in alternative embodiments. Arrays of transducers may be functionalized with MOFs or sensing materials having different properties so that the sensor array can sensitively detect and differentiate multiple target analytes, chemical compounds, and even complex mixtures. Also, the sensor device includes at least one pressure sensor for sensing the ambient or atmospheric pressure in some embodiments. The ambient or atmospheric pressure should not be confused with the partial pressure of a target gas, which term partial pressure we are using as synonymous with the concentration of the target gas. An ambient pressure sensor may be useful for applications of the sensor device in which the ambient or atmospheric pressure may differ from standard atmospheric pressure, and adjustments to the calculation of the concentration of the target gas may include ambient pressure measurements.

In presently preferred embodiments, the sensing material is from a family of porous metal-organic framework materials known as amine-appended $M_2$(DOBPDC). Other suitable sensing materials may be possible in other embodiments, in particular other MOFs may be suitable. In general, a sensing material for $CO_2$ should exhibit at least 0.1 wt % uptake of $CO_2$ across the active sensor range (e.g., 400 to 2,000 ppm). The gas uptake or desorption preferably occurs in a "step" change such that, at a temperature T, as $CO_2$ concentration increases from 400 ppm to 2,000 ppm, at least 25%, and more preferably at least 50%, of the total $CO_2$ mass uptake observed over the total active sensor range occurs within a much narrower "range" (e.g., less than or equal to 10% of the total concentration range or temperature range of the sensor device). By changing the temperature of the sensing material, the concentration at which the step change (or inflection point) occurs also changes.

More generally, for a target gas (not necessarily $CO_2$) to be sensed, the sensing material should take up at least 0.1 wt % of the target gas across a defined range of concentration, $C_{min}$ to $C_{max}$, for that gas. The concentration range is preferably equal to or greater than the desired sensing range of the device. In other words, there is a temperature, $T_{min}$, at which the range of the step includes concentration $C_{min}$. Moreover, there is a temperature, $T_{max}$, at which the range of the step includes concentration $C_{max}$. Thus, by setting a temperature between $T_{min}$ and $T_{max}$, the step can be moved to any point between concentrations $C_{min}$ and $C_{max}$. The uptake of target gas in the sensing material preferably occurs in a "step" change such that, at temperature T, as the concentration of the target gas increases from $C_{min}$ to $C_{max}$, at least 25%, and more preferably at least 50% of the total mass uptake over the total concentration range occurs within a narrower range that is much smaller than the total concentration range or total temperature range (e.g., preferably less than or equal to 10% of the total concentration or temperature range of the sensor device). By changing the temperature of the sensing material, the concentration at which the inflection point or step change in uptake occurs also changes. In some embodiments, the sensing material provides a very steep "step" change, so that about 70% to 90% of the gas uptake observed over the total active sensor range occurs within a much narrower "range" (e.g., less than less than or equal to 10% of the total concentration range or temperature range of the sensor device).

Although the above embodiments describe mmen-$Mg_2$(DOBPDC) or amine-appended $M_2$(DOBPDC) as a preferred sensing material, many other sensing materials (preferably MOFs) may be used in alternative embodiments. Also, although a step change in uptake and a corresponding step change in the transducer measurement signal values is described as a simple and useful example of a signal value condition to be satisfied, there are many other signal value conditions suitable for use in the sensor device. For example, in some embodiments, the signal value condition is satisfied at an inflection point on a curve defined by, derived from, or fitted to the values of the transducer measurement signals. The processor may be programmed to determine the inflection point by finding a maximum of the first derivative of the curve with respect to gas concentration, as previously described with reference to FIGS. 4A and 4B. In some embodiments, the processor may be programmed to determine the inflection point by finding a minimum of the first derivative of the curve with respect to temperature. Such an embodiment will now be described.

Figure 9:
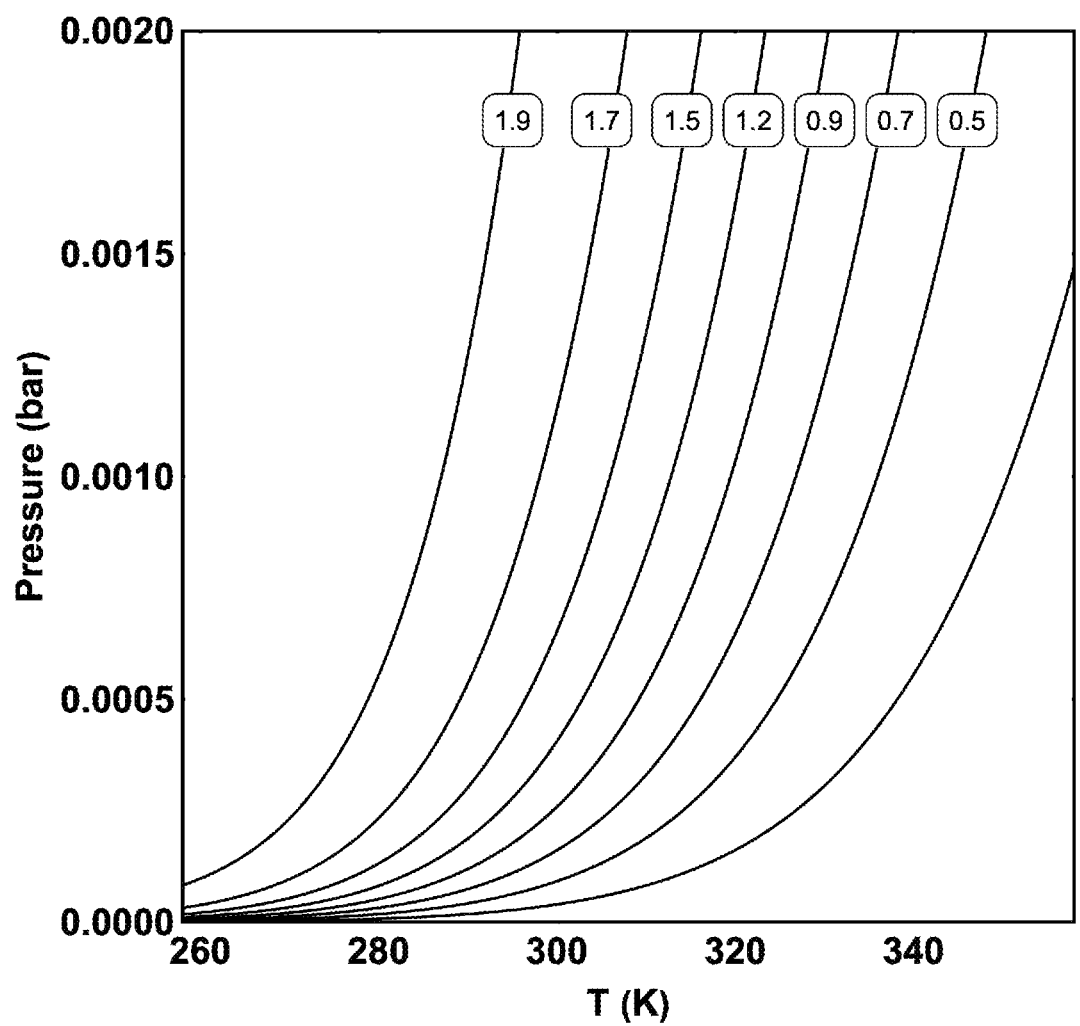
FIG. 9 is a graph showing curves of partial pressure of a target gas (i.e., gas concentration) as a function of temperature (Kelvin). Rounded rectangles on each curve represent gas uptake (mmol/g) of the target gas in the film of sensing material.

FIG. 9 is a graph showing curves of partial pressure of a target gas (e.g., $CO_2$) as a function of temperature (Kelvin). Rounded rectangles on each curve represent gas uptake (mmol/g) of the target gas in the film of sensing material. The term "pressure" here refers to the partial pressure of the gas, and is interchangeable with the gas concentration. This graph represents an arbitrary MOF, not necessarily mmen-$Mg_2$(DOBPDC) or amine-appended $M_2$(DOBPDC) as a preferred sensing material. The graph captures all of the variables we use to determine concentration of the target gas. The gas concentration is set by the environment and is the quantity to be determined. The temperature may be controlled in any of the three ways previously described such as a temperature range (e.g., sweep or oscillate through the range), setpoint temperature corresponding to a target concentration for an alarm embodiment, or temperature change according to a servomechanism. An example of input that could be used to govern the servomechanism is the uptake amount. This is similar to the setpoint frequency embodiment previously described, since the transducer frequency is often proportional or inversely proportional to the uptake amount. For example, if we wanted to maintain uptake at about 1.2 mmol/g, and the uptake is found to be <0.5 mmol/g, then the device would switch into cooling mode until the setpoint uptake of 1.2 mmol/g is reached, whereas if gas uptake were found to be >1.5 mmol/g, then the sensor device would switch into heating mode. From this graph, we can extract two-dimensional curves that are either at constant temperature (isotherms) or constant partial pressure (isobars).

Figure 10:
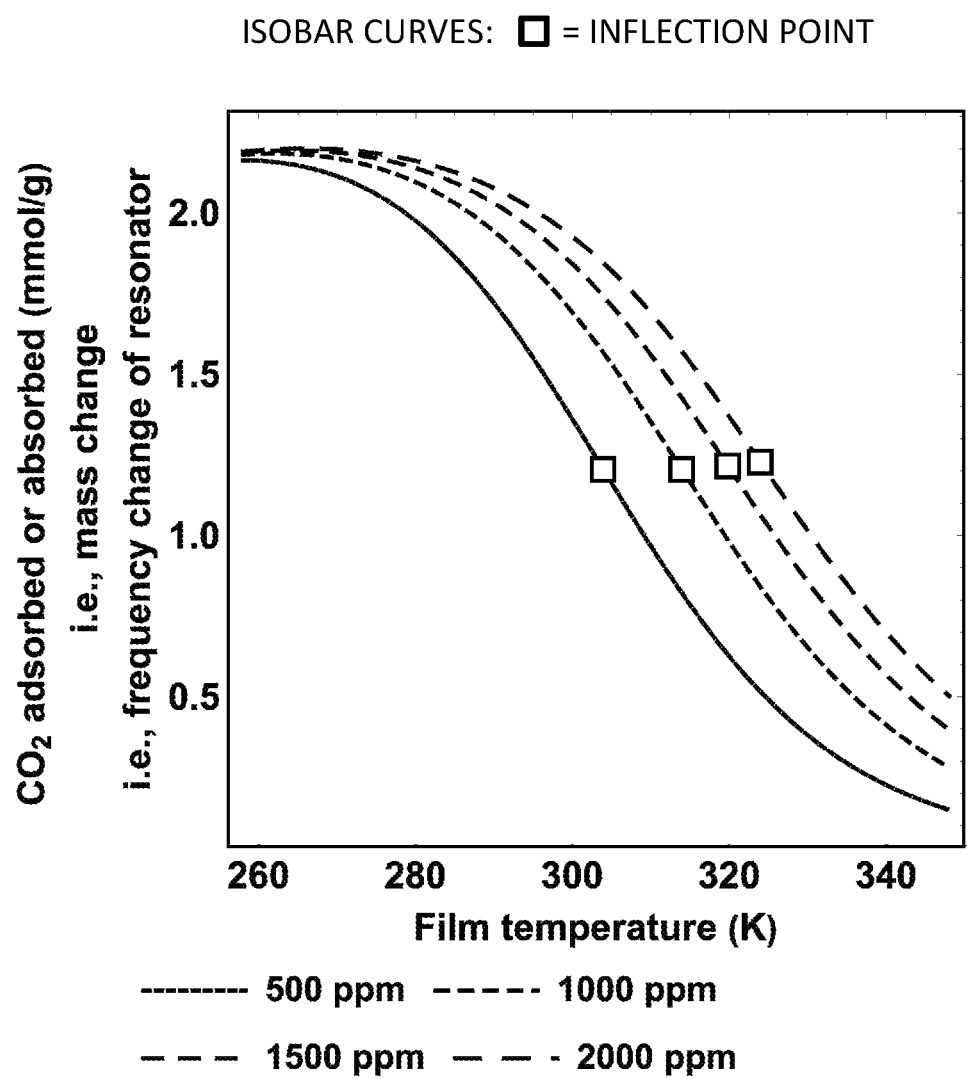
FIG. 10 is a graph showing gas uptake (i.e. transducer signal values) as a function of temperature (Kelvin). Square symbols on each isobaric curve represent inflection points.

FIG. 10 is a graph showing isobars with gas uptake (i.e. transducer signal values) as a function of temperature (Kelvin). Squares on each isobaric curve represent inflection points. We can identify an inflection point as a minimum of the first derivative of each curve with respect to temperature. The temperature of the sensing material at the inflection point is used to determine the concentration of $CO_2$ with good accuracy (e.g., by calibration curves or look-up table). In a particularly useful "servo" embodiment, the amplitude of the temperature sweeps is limited to a region around the inflection point. The principle is the same as in the "sweep" embodiment, but the temperature sweep window may be updated continuously to find the inflection point as the gas concentration in the environment changes.

According to some embodiments, the present invention provides, inter alia, computer systems comprising hardware (e.g. one or more processors and associated memory) programmed to perform the methods described herein, as well as computer-readable media encoding instructions to perform the methods described herein. In some embodiments, a look-up table or calibration curve is used to determine the quantity (e.g., concentration, partial pressure, or mass) of each substance of interest (e.g., $CO_2$), according to the signals or data indicating the transducer responses (e.g., frequencies). The look-up table or calibration data may be in one or more processors and associated memory included with the sensor device. In some embodiments, an on-board microprocessor is programmed to store measured signal values and/or to determine gas quantities or values. Alternatively, these functions may be performed in a separate processor or external computer in communication with the sensor portion of the device, with or without wires. Wireless communication between devices is well known in the art. In other embodiments, the sensor has only some signal processing electronics, and some determination and calculation functions are performed in a separate processor or external computer in communication with the sensor. Alternatively, multiple processors may be provided, e.g., providing one or more signal processing electronics or microprocessors in the sensor that communicate (wirelessly or with wires) with one or more external processors or computers. Although a single controller or processor is described in the above embodiments for simplicity in patent drawings, it is to be understood that the sensor device may include multiple processors and/or associated memories. In some embodiments, at least one on-board microprocessor or controller receives transducer measurement signals/data and temperature measurement signals/data from the detector and the temperature sensor, respectively, either through direct connections or indirectly through one or more additional signal processing circuits or processor components.

Accordingly, the scope of the invention should be determined by the following claims and their legal equivalents.

What is claimed is:

1. A sensor device for detecting at least one target gas, the device comprising:
   a) at least one transducer;
   b) a sensing material disposed on the transducer, wherein the sensing material has an ability to adsorb or absorb an amount of the target gas that depends on a temperature of the sensing material and a concentration or partial pressure of the target gas;
c) at least one detector arranged to detect responses of the transducer to sorption or desorption of the target gas in the sensing material and to output transducer measurement signals indicative of the responses of the transducer;
d) at least one thermal element arranged to change the temperature of the sensing material by heating and/or cooling;
e) a temperature sensor arranged to measure a temperature of the sensing material; and
f) at least one processor in communication with the detector and the temperature sensor, wherein the processor is programmed to determine a quantity of the target gas according to the temperature of the sensing material at which the transducer measurement signals satisfy a signal value condition.

2. The device of claim 1, wherein the signal value condition is satisfied at an inflection point on a curve defined by, derived from, or fitted to the values of the transducer measurement signals, or wherein the signal value condition is satisfied at an extremum of a first derivative of the curve, or at a zero-crossing of a second derivative of the curve.

3. The device of claim 1, wherein the signal value condition is satisfied at a point on a curve defined by, derived from, or fitted to the values of the transducer measurement signals where the absolute value of the slope of the curve is greater than or equal to a threshold value, or where the absolute value of a first derivative of the curve is greater than or equal to the threshold value.

4. The device of claim 1, wherein the signal value condition is satisfied if the transducer measurement signals indicate a step change in the amount of the target gas adsorbed or absorbed in the sensing material.

5. The device of claim 4, wherein the processor is programmed to determine whether the step change occurs by comparing the change in the values of the transducer measurement signals to a minimum step height within a temperature range or gas concentration range that is narrower than a maximum step width.

6. The device of claim 1, wherein the signal value condition is satisfied if the values of the transducer measurement signals have a rate of change with respect to temperature or gas concentration that is greater than or equal to a threshold value, or if the rate of change is a maximum.

7. The device of claim 1, wherein the sensing material is a porous coordination polymer.

8. The device of claim 1, wherein the sensing material is a metal-organic framework material comprising mmen-$Mg_2$(DOBPDC) or amine-appended $M_2$(DOBPDC).

9. The device of claim 1, further comprising at least one temperature control circuit connected to the thermal element and the processor, wherein the processor is further programmed to initiate heating or cooling of the sensing material to vary the temperature of the sensing material over a temperature range having a center temperature and an amplitude, and the center temperature is selected according to a target concentration of the gas or according to at least one previously determined quantity of the target gas.

10. The device of claim 1, wherein the quantity to be determined by the processor is a target concentration of the gas for an alarm signal, the device further comprises a temperature control circuit connected to the thermal element and the processor, the processor is further programmed to determine a setpoint temperature for the sensing material corresponding to the target concentration of the gas, to initiate heating or cooling of the sensing material to the setpoint temperature, and to initiate an alarm signal if the signal value condition is satisfied at the setpoint temperature, and wherein the sensing material has a temperature-dependent gas sorption behavior so that the signal value condition is satisfied at the setpoint temperature only if the target gas is present at about the target concentration.

11. The device of claim 1, wherein the transducer comprises a resonant mass transducer, the transducer measurement signals are indicative of detected frequency, and the device further comprises at least one temperature control feedback loop, connected to the thermal element and under control of the processor, to change the temperature of the sensing material according to the detected frequency such that the operating frequency of the transducer is maintained around a substantially constant setpoint frequency.

12. A method for detecting at least one target gas in an environment or sample, the method comprising:
a) changing the temperature of a sensing material disposed on at least one transducer, wherein the sensing material has an ability to adsorb or absorb an amount of the target gas that depends on a temperature of the sensing material and a concentration or partial pressure of the target gas;
b) detecting responses of the transducer to sorption or desorption of the target gas in the sensing material;
c) outputting transducer measurement signals indicative of the responses of the transducer; and
d) utilizing at least one processor to determine a quantity of the target gas according to the temperature of the sensing material at which the transducer measurement signals satisfy a signal value condition.

13. The method of claim 12, wherein the signal value condition is satisfied at an inflection point on a curve defined by, derived from, or fitted to the values of the transducer measurement signals, or wherein the signal value condition is satisfied at an extremum of a first derivative of the curve, or at a zero-crossing of a second derivative of the curve.

14. The method of claim 12, wherein the signal value condition is satisfied at a point on a curve defined by, derived from, or fitted to the values of the transducer measurement signals where the absolute value of the slope of the curve is greater than or equal to a threshold value, or where the absolute value of a first derivative of the curve is greater than or equal to the threshold value.

15. The method of claim 12, wherein the signal value condition is satisfied if the transducer measurement signals indicate a step change in the amount of the target gas adsorbed or absorbed in the sensing material.

16. The method of claim 15, wherein the processor determines if the step change occurs by comparing the change in the values of the transducer measurement signals to a minimum step height within a temperature range or concentration range that is narrower than a maximum step width.

17. The method of claim 12, wherein the signal value condition is satisfied if the values of the transducer measurement signals have a rate of change with respect to temperature or gas concentration that is greater than or equal to a threshold value, or the signal value condition is satisfied if the rate of change is a maximum.

18. The method of claim 12, wherein the sensing material is a porous coordination polymer.

19. The method of claim 12, wherein the sensing material is a metal-organic framework material comprising mmen-$Mg_2$(DOBPDC) or amine-appended $M_2$(DOBPDC).

20. The method of claim 12, wherein the temperature of the sensing material is swept through a temperature range having a center temperature and an amplitude, and the center temperature is selected according to a target concentration of the gas or according to at least one previously determined quantity of the target gas.

21. The method of claim 12, wherein the quantity to be determined is a target concentration of the gas for an alarm signal, the processor is further utilized to determine a setpoint temperature for the sensing material corresponding to the target concentration of the gas, to initiate heating or cooling of the sensing material to the setpoint temperature, and to initiate an alarm signal if the signal value condition is satisfied at the setpoint temperature, and wherein the sensing material has a temperature-dependent gas sorption behavior so that the signal value condition is satisfied at the setpoint temperature only if the target gas is present at about the target concentration.

22. The method of claim 12, wherein the transducer comprises a resonant mass transducer, the transducer measurement signals are indicative of detected frequency, and the temperature of the sensing material is changed according to the detected frequency such that the operating frequency of the transducer is maintained around a substantially constant setpoint frequency.

* * * * *